United States Patent
Tsai

(10) Patent No.: US 6,423,033 B1
(45) Date of Patent: Jul. 23, 2002

(54) SAFETY HYPODERMIC SYRINGE

(76) Inventor: Jin-Chou Tsai, 18F, No. 95, Roosevelt Rd., Sec. 2, Taipei City (TW)

( * ) Notice: Subject to any disclaimer, the term of this patent is extended or adjusted under 35 U.S.C. 154(b) by 0 days.

(21) Appl. No.: 09/796,514

(22) Filed: Mar. 2, 2001

(51) Int. Cl.[7] .............................................. A61M 29/00
(52) U.S. Cl. ...................................... 604/110; 604/187
(58) Field of Search ................................. 604/110, 187, 604/195, 197, 198, 218

(56) References Cited

U.S. PATENT DOCUMENTS

| | | | | |
|---|---|---|---|---|
| 5,047,017 A | * | 9/1991 | Koska | 604/110 |
| 5,290,255 A | * | 3/1994 | Vallelunga et al. | 604/110 |
| 5,344,403 A | * | 9/1994 | Lee | 604/110 |
| 5,395,346 A | * | 3/1995 | Maggioni | 604/110 |
| 5,415,648 A | * | 5/1995 | Malay et al. | 604/110 |
| 5,820,605 A | * | 10/1998 | Zdeb et al. | 604/110 |

* cited by examiner

*Primary Examiner*—Lesley D. Morris
*Assistant Examiner*—John Fristoe
(74) *Attorney, Agent, or Firm*—Rosenberg, Klein & Lee

(57) ABSTRACT

A safety hypodermic syringe in which a pull handle is inserted into the plunger and adapted to pull the needle assembly backwards to the inside of the plunger in the barrel after the service of the safety hypodermic syringe. The pull handle has a middle neck through which the rear part of the pull handle can easily be separated from the front part of the pull handle by bending, enabling the separated rear part of the pull handle to be inserted into the plunger in the barrel and hooked up with the front part of the pull handle.

7 Claims, 5 Drawing Sheets

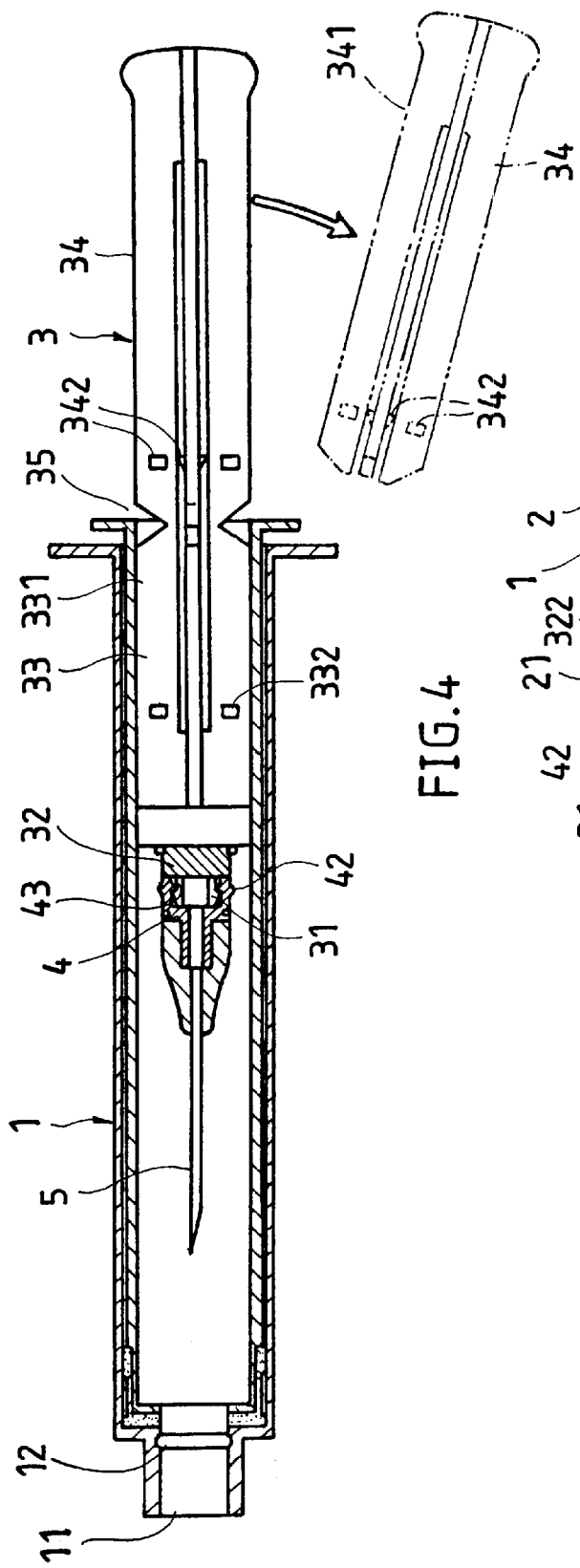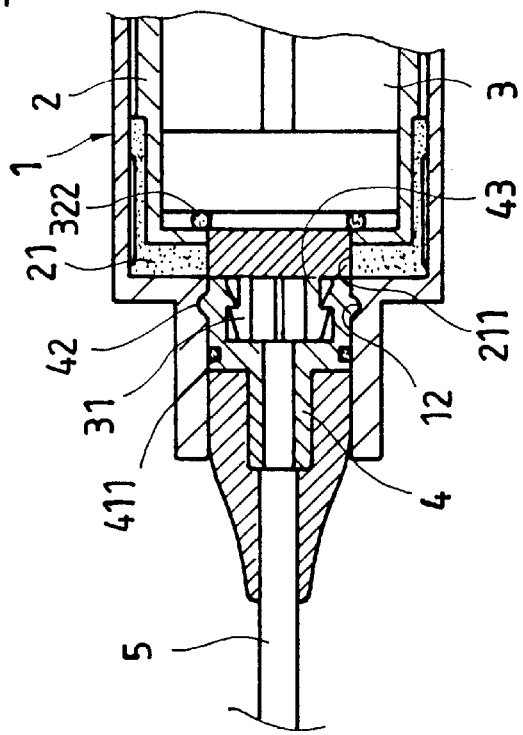
FIG.4
FIG.3

SAFETY HYPODERMIC SYRINGE

BACKGROUND OF THE INVENTION

The present invention relates to hypodermic syringes and, more particularly, to a safety hypodermic syringe, which enables the needle assembly to be received inside the plunger in the barrel after the service of the safety hypodermic syringe.

Hypodermic syringes must be collected and properly disposed of after their service to prevent possible contamination and transmission of diseases, for example, AIDS, hepatitis, etc. However, because the needle cannula is disposed outside the barrel after the service of the hypodermic syringe, the medical person who settles the waste hypodermic syringe tends to be injured by the needle cannula when handling the waste hypodermic syringe. In order to prevent direction contact of the hands with the needle cannula of a waste hypodermic syringe, a protective cap may be used and covered on the needle assembly. However, this method is not perfect because the protective cap tends to be forced out of the needle assembly by an external force. There is known a safety hypodermic syringe, which enables the needle assembly to be pulled backwards with the plunger and received inside the barrel after the service of the safety hypodermic syringe. However, because the plunger is separated from the needle assembly and removed from the barrel and cannot be inserted into the barrel again after the needle assembly has been received inside the barrel, much storage space is required for the used safety hypodermic syringe. There is known another structure of safety hypodermic syringe in which the plunger has a front hook, which hooks on a part of the needle assembly after the service of the safety hypodermic syringe, for enabling the needle assembly to be pulled backwards with the plunger and received inside the barrel in a tilted position. However, because the plunger has a part extended out of the rear side of the barrel after the needle assembly has been received inside the barrel in a tilted position, the plunger and the needle assembly tends to be pulled out of the barrel accidentally.

SUMMARY OF THE INVENTION

The present invention has been accomplished to provide a safety hypodermic syringe, which eliminates the aforesaid drawbacks. It is one object of the present invention to provide a safety hypodermic syringe, which enables the needle assembly to be received inside the plunger within the barrel after the service of the safety hypodermic syringe. It is another object of the present invention to provide a safety hypodermic syringe, which has parts received one within another to minimize storage space after the service. The safety hypodermic syringe of the invention comprises a barrel, a needle assembly mounted in a front neck of the barrel, a tubular plunger with a rubber stopper inserted into the barrel, and a pull handle inserted into the plunger and adapted to pull the needle assembly backwards to the inside of the plunger in the barrel after the service of the safety hypodermic syringe. The pull handle has a middle neck through which the rear part of the pull handle can easily be separated from the front part of the pull handle by bending, enabling the separated rear part of the pull handle to be inserted into the plunger in the barrel and hooked up with the front part of the pull handle.

BRIEF DESCRIPTION OF THE DRAWINGS

FIG. 3 is a sectional view in an enlarged scale of a part of the present invention, showing the cylindrical, flanged, split retaining bolt of the pull handle forced into engagement with the needle holder.

FIG. 4 is a schematic drawing showing the needle holder and the needle cannula pulled backwards with the pull handle to the inside of the tubular plunger in the barrel after the service of the safety hypodermic syringe and the separation action of the rear handle body of the pull handle from the front handle body.

FIG. 6 is a perspective view of a part of an alternate of the pull handle according to the present invention.

DETAILED DESCRIPTION OF THE PREFERRED EMBODIMENT

Figure 1:
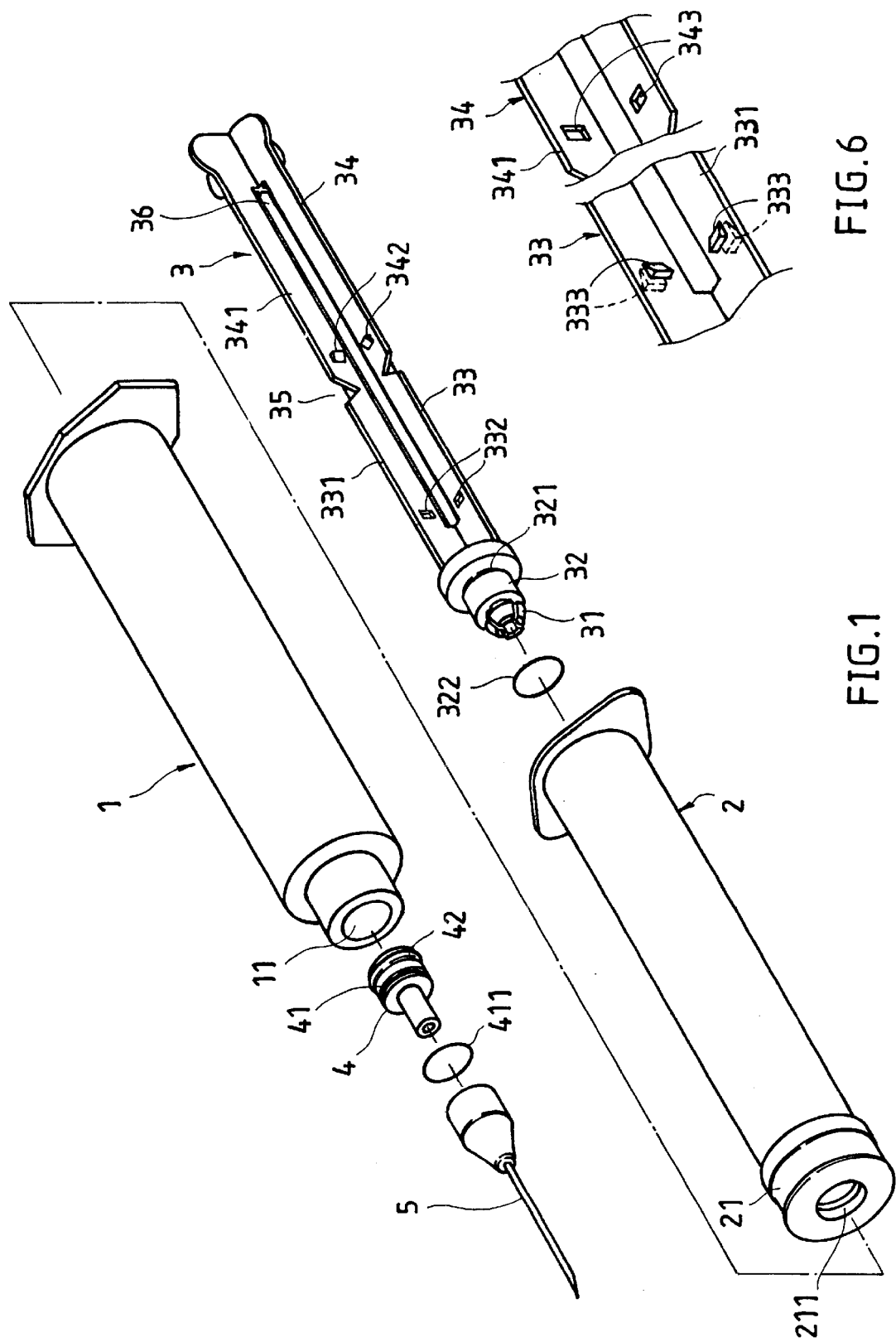
FIG. 1 is an exploded view of a safety hypodermic syringe constructed according to one embodiment of the present invention.
Figure 2:
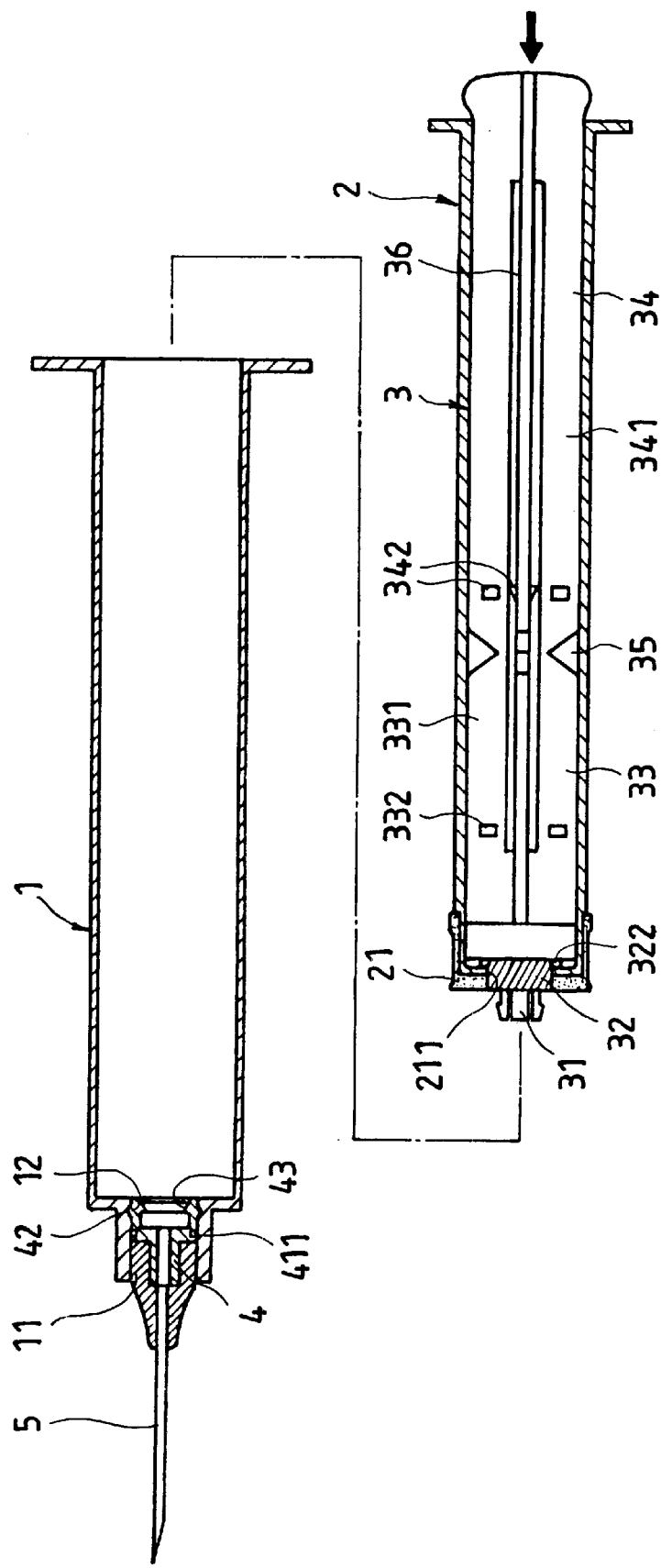
FIG. 2 is a sectional view of the present invention before the insertion of the tubular plunger with the pull handle into the barrel.
Figure 5:
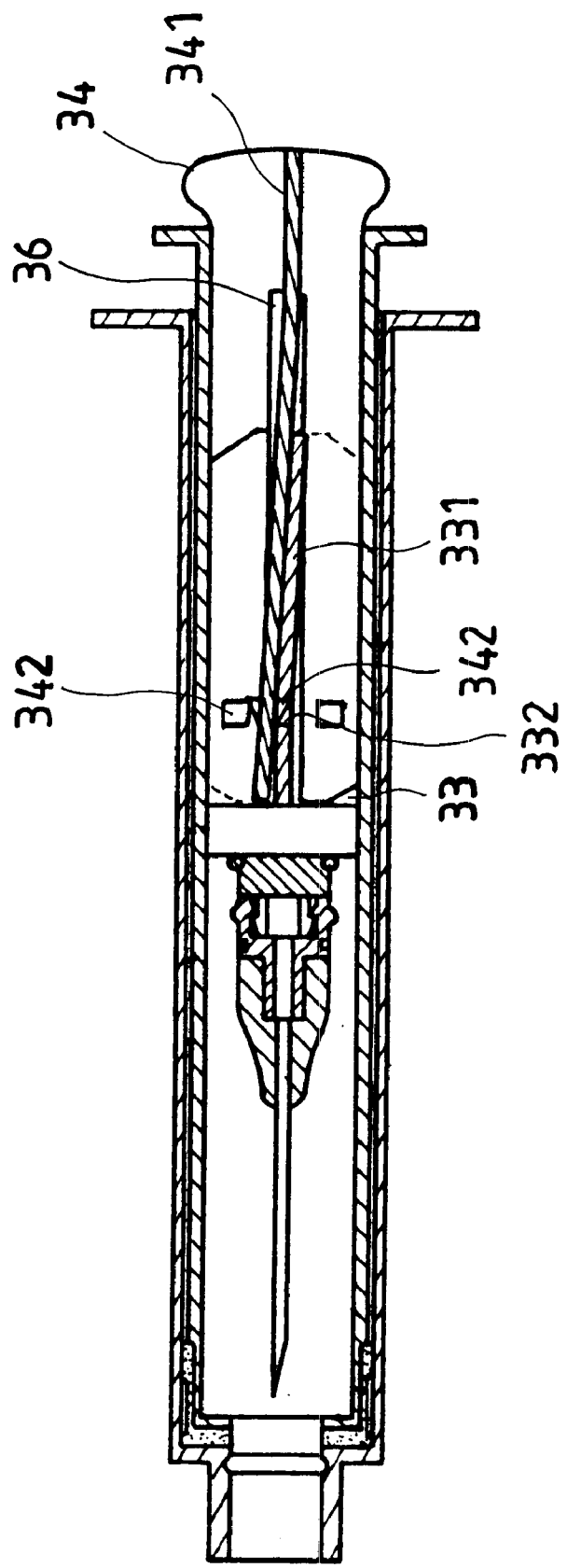
FIG. 5 is a sectional view of the present invention showing the needle holder and the needle cannula received inside the tubular plunger in the barrel, the rear handle body separated from the pull handle and fastened to the front handle body in the tubular plunger.

Referring to FIGS. from 1 through 5, a safety hypodermic syringe is shown comprising a barrel 1, a plunger 2, a pull handle 3, a needle holder 4, and a needle cannula 5. The barrel 1 has a front neck 11, and an annular inside locating groove 12 extended around the inside wall of the front neck 11. The plunger 2 is a tubular member inserted into the barrel 1 from the rear side, having a rubber stopper 21 fixedly provided at the front side thereof. The rubber stopper 21 has a center through hole 211 disposed in communication with the inner diameter of the plunger 2. The pull handle 3 is inserted into the tubular plunger 2 from the rear side, comprising a front neck 32 fitted into the center through hole 211 of the rubber stopper 21 of the tubular plunger 2, a cylindrical, flanged, split retaining bolt 31 axially forwardly extended from the front neck 32 and suspended outside the tubular plunger 2 in front of the rubber stopper 21, an annular outside groove 321 disposed around the periphery of the front neck 32, and a rubber seal ring 322 mounted in the annular outside groove 321 around the periphery of the front neck 32 of the pull handle 3 and stopped against the peripheral wall of the center through hole 211 of the rubber stopper 21 of the tubular plunger 2. The needle cannula 5 is fastened to the needle holder 4, and then mounted with the needle holder 4 in the front neck 11 of the barrel 1.The needle holder 4 fits the inner diameter of the front neck 11 of the barrel 1, comprising an annular outside locating flange 42 forced into engagement with the annular inside locating groove 12 of the barrel 1, an annular outside groove 41 disposed around the periphery, a rubber seal ring 411 mounted in the annular outside groove 41 and stopped against the inside wall of the front neck 11 of the barrel 1, and a hook 43 disposed around the inner diameter thereof. During injection, the pull handle 3 is pushed forwards with the tubular plunger 2 to eject medicine out of the tubular barrel 1 into the body of the patient through the needle holder 4 and the needle cannula 5. After the pull handle 3 and the tubular plunger 2 have been pushed to the front limit position in the barrel 1, the retaining bolt 31 of the pull handle 3 is forced into the inside of the needle holder 4 and engaged with the hook 43, so that the needle holder 4 and the needle cannula 5 are carried backwards to the inside of the tubular plunger 2 within the barrel 1 when pulling the pull handle 3 out of the back side of the barrel 1. The pull handle 3 has a middle neck 35, which divides the pull handle 3 into a front handle body 33 and a rear handle body 34, a longitudinal slot 36 longitudinally extended on the middle, and a plurality of radial ribs 331 and 341 spaced around the longitudinal slot 36. Through the middle neck 35, the pull handle 3 can easily be broken to separate the rear handle body 34 from the front handle body 33. The radial ribs 331 of the front handle body 33 each have a hook hole 332. The radial ribs 341 of the rear handle body 34 each have a hooked portion 342. After the service of the safety hypodermic syringe, the pull handle 3 is pulled out of the tubular plunger 2 to move the needle holder 4 and the needle cannula 5 backwards to the inside of the tubular plunger 2 within the barrel 1, and then the pull handle 3 is bent in one direction to break the middle neck 35 and to separate the rear handle body 34 from the front handle body 33, and then the separated rear handle body 34 is inserted into the tubular plunger 2 and closely attached to the front handle body 33, enabling the hooked portions 342 of the rear handle body 34 to be respectively forced into engagement with the hook holes 332 of the front handle body 33 (see FIGS. 4 and 5). Thus the size of the used safety hypodermic syringe is greatly reduced.

Referring to FIG. 6, as an alternate form of the present invention, hooked portions 33 are respectively provided at the radial ribs 331 of the front handle body 33, and retaining holes 343 are respectively provided at the radial ribs 341 of the rear handle body 34. After separation of the rear handle body 34 from the front handle body 33, the rear handle body 34 is attached to the front handle body 33 to force the retaining holes 343 into engagement with the hooked portions 333 respectively.

Figure 7:
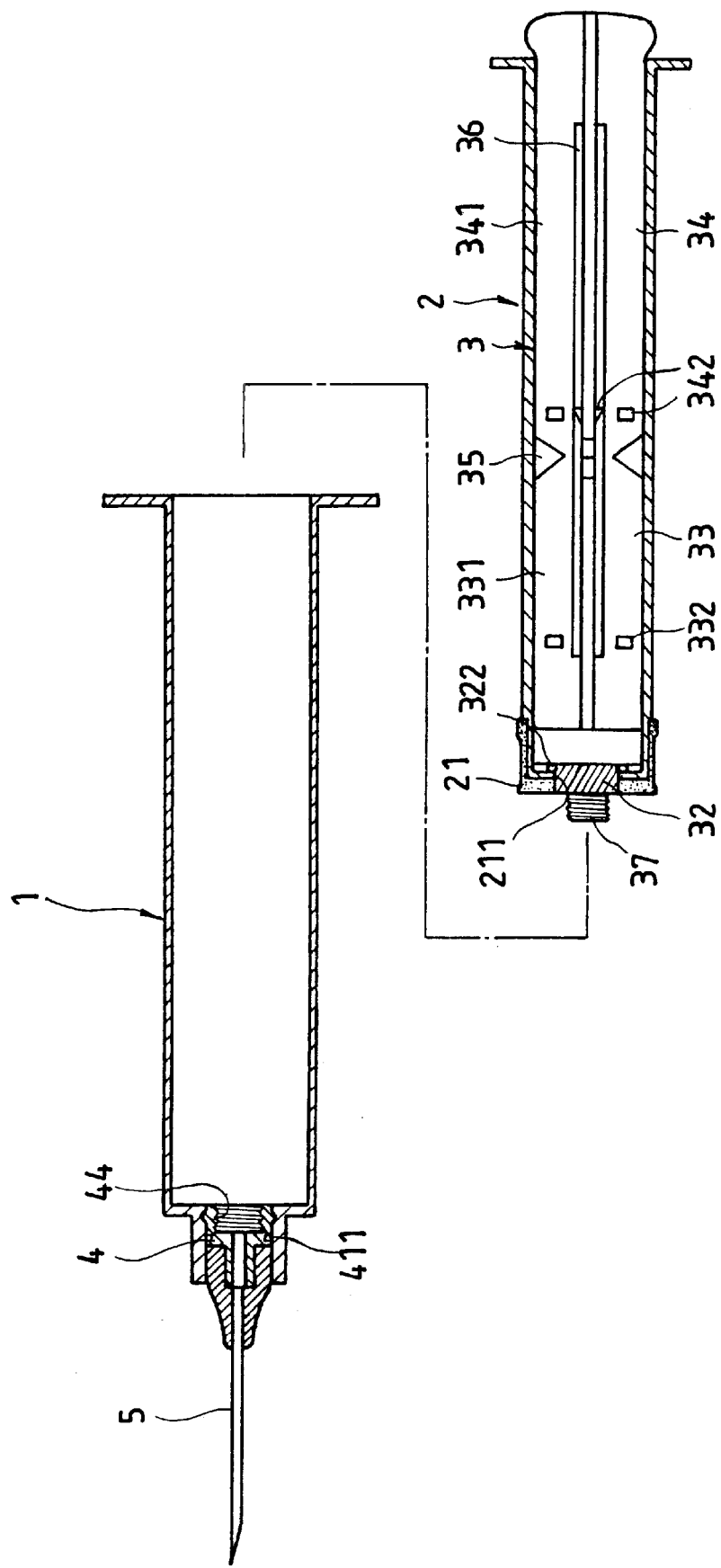
FIG. 7 is a sectional view of another alternate form of the present invention.

FIG. 7 shows another alternate form of the present invention. According to this alternate form, the needle holder 4 has an inner thread 44 at the rear side thereof, and the pull handle 3 has a front screw rod 37 axially forwardly extended from the front neck 32 and adapted for threading into the inner thread 44 of the needle holder 4. After the service of the safety hypodermic syringe, the pull handle 3 is rotated to thread the front screw rod 37 into the inner thread 44 of the needle holder 4, for enabling the needle holder 4 and the needle cannula 5 to be pulled backwards to the inside of the tubular plunger 2 in the barrel 1 upon backward movement of the pull handle 3.

A prototype of safety hypodermic syringe has been constructed with the features of the annexed drawings. The safety hypodermic syringe functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A safety hypodermic syringe comprising:
   a barrel, said barrel having a front neck and an inside locating groove inside the front neck of said barrel;
   a needle holder fitted into the front neck of said barrel and holding a needle cannula outside said barrel, said needle holder comprising an annular outside locating flange forced into engagement with the annular inside locating groove of said barrel, an annular outside groove disposed around the periphery thereof, and a rubber seal ring mounted in the annular outside groove of said needle holder and stopped against an inside wall of the front neck of said barrel;
   a tubular plunger inserted into said barrel, said tubular plunger having a rubber stopper fixedly provided at a front side thereof, said rubber stopper having a center through hole; and
   a pull handle inserted into said tubular plunger, said pull handle comprising a front handle body, a rear handle body, a middle neck connected between said front handle body and said rear handle body, said middle neck being breakable upon bending of said rear handle body relative to said front handle body, for enabling said rear handle body to be separated from said front handle body, and a front neck axially forwardly extended from a front side of said front handle body remote from said rear handle body and press-fitted into the center through hole of said rubber stopper of said tubular plunger; and
   fastening means provided at the front neck of said pull handle and said needle holder for enabling said needle holder and said needle cannula to be secured to the front neck of said pull handle and moved with said pull handle backwardly to the inside of said tubular plunger in said barrel after the service of the safety hypodermic syringe.

2. The safety hypodermic syringe of claim 1 wherein said fastening means comprises a cylindrical, flanged, split retaining bolt axially forwardly extended from the front neck of said pull handle and suspended outside said tubular plunger in front of said rubber stopper, and a hook disposed around an inside wall of said needle holder and adapted to engage said cylindrical, flanged, split retaining bolt after said pull handle has been pushed with said tubular plunger to a front side of said barrel, for enabling said needle holder and said needle cannula to be pulled backwardly with said pull handle to the inside of said tubular plunger in said barrel.

3. The safety hypodermic syringe of claim 1 wherein said fastening means comprises a screw rod axially forwardly extended from the front neck of said pull handle and suspended outside said tubular plunger in front of said rubber stopper, and an inner thread disposed around an inside wall of said needle holder for engagement with said cylindrical, flanged, split retaining bolt after said pull handle has been pushed with said tubular plunger to a front side of said barrel and rotated in one direction, for enabling said needle holder and said needle cannula to be pulled backwardly with said pull handle to the inside of said tubular plunger in said barrel.

4. The safety hypodermic syringe of claim 1 wherein the front neck of said pull handle comprises an outside annular groove disposed around the periphery thereof, and a rubber seal ring mounted in the outside annular groove around the periphery of the front neck of said pull handle and stopped against the peripheral wall of the center through hole of said rubber stopper of said tubular plunger.

5. The safety hypodermic syringe of claim 1 wherein said plunger comprises a longitudinal slot extended through said middle neck, a plurality of first radial ribs provided at said front handle body around said longitudinal slot, and a plurality of radial ribs provided at said rear handle body around said longitudinal slot.

6. The safety hypodermic syringe of claim 5 wherein said first radial rids each have a hook hole, and said second radial ribs each have a hooked portion adapted for hooking in the hook hole on each of said first radial rib upon attaching of said rear handle body to said front handle body after separation of said rear handle body from said front handle body.

7. The safety hypodermic syringe of claim 5 wherein said first radial rids each have a hooked portion, and said second radial ribs each have a hook hole adapted to receive the hooked portion of each of said first radial rib upon attaching of said rear handle body to said front handle body after separation of said rear handle body from said front handle body.

* * * * *